United States Patent
Takada

(10) Patent No.: US 9,333,326 B2
(45) Date of Patent: *May 10, 2016

(54) GUIDEWIRE

(71) Applicant: ASAHI INTECC CO., LTD., Nagoya-shi, Aichi (JP)

(72) Inventor: Keigo Takada, Sakai (JP)

(73) Assignee: ASAHI INTECC CO., LTD., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/314,432

(22) Filed: Jun. 25, 2014

(65) Prior Publication Data

US 2015/0088101 A1    Mar. 26, 2015

(30) Foreign Application Priority Data

Sep. 25, 2013   (JP) ................................ 2013-197686

(51) Int. Cl.
*A61B 5/00*   (2006.01)
*A61M 25/00*   (2006.01)
*A61M 25/09*   (2006.01)

(52) U.S. Cl.
CPC ..... *A61M 25/09* (2013.01); *A61M 2025/09083* (2013.01); *A61M 2025/09091* (2013.01); *A61M 2025/09133* (2013.01)

(58) Field of Classification Search
CPC ................... A61M 25/09; A61M 2025/09083; A61M 2025/09091; A61M 2025/09133
See application file for complete search history.

(56) References Cited

U.S. PATENT DOCUMENTS

| 5,840,046 | A | 11/1998 | Deem |
| 6,340,441 | B1 | 1/2002 | Meyer et al. |
| 7,553,287 | B2 * | 6/2009 | Reynolds et al. ............. 600/585 |
| 8,480,598 | B2 * | 7/2013 | Nelson, III ............ A61M 25/09 |
| | | | 600/434 |
| 2005/0096567 | A1 | 5/2005 | Reynolds et al. |
| 2006/0047224 | A1 | 3/2006 | Grandfield |

(Continued)

FOREIGN PATENT DOCUMENTS

| EP | 0820782 A2 | 1/1998 |
| EP | 0 982 046 A1 | 3/2000 |

(Continued)

OTHER PUBLICATIONS

Aug. 27, 2014 Extended Search Report issued in European Patent Application No. 14173723.9.
Jan. 7, 2016 Office Action issued in European Patent Application No. 14 173 723.9.

(Continued)

*Primary Examiner* — Devin Henson
(74) *Attorney, Agent, or Firm* — Oliff PLC

(57) ABSTRACT

A guide wire has a coil body covered with a hydrophilic coating film that exhibits sufficient lubricity even when there is little moisture in its surroundings. In the coil-type guide wire, a coating portion is formed by a plurality of layers where the innermost layer includes a hydrophobic film and an outer layer includes a hydrophilic film. Portions of the innermost layer extend between adjacent coils of the coil body and spaces are formed between the outer layer thereof and the portions of the innermost layer between the coils. The spaces allow moisture to pool so that when moisture in the guide wire's surroundings decreases, it is possible to supply the moisture pooled in the spaces to the hydrophilic film. Thus, even when there is little moisture in the guide wire's surroundings, it is possible to have a sufficient amount of lubricity.

3 Claims, 5 Drawing Sheets

(56) References Cited

U.S. PATENT DOCUMENTS

| | | | |
|---|---|---|---|
| 2008/0004546 A1* | 1/2008 | Kato | A61M 25/09 600/585 |
| 2008/0183812 A1 | 7/2008 | Paul et al. | |
| 2011/0245729 A1 | 10/2011 | Satozaki | |
| 2011/0245730 A1* | 10/2011 | Satozaki | 600/585 |

FOREIGN PATENT DOCUMENTS

| | | |
|---|---|---|
| EP | 1 243 283 A2 | 9/2002 |
| EP | 1498152 A1 | 1/2005 |
| EP | 1 875 941 A1 | 1/2008 |
| EP | 2 371 402 A2 | 10/2011 |
| JP | 2007509713 A | 4/2007 |
| JP | 2008011938 A | 1/2008 |
| JP | A-2008-237621 | 10/2008 |
| JP | 2011206494 A | 10/2011 |
| WO | 97/48330 A1 | 12/1997 |
| WO | 2004/007014 A1 | 1/2004 |

OTHER PUBLICATIONS

Dec. 17, 2014 Search Report issued in European Application No. 14173724.7.
Oct. 27, 2015 Office Action issued in Japanese Application No. 2013-197685.
Oct. 27, 2015 Office Action issued in Japanese Application No. 2013-197686.
Oct. 27, 2015 Office Action issued in Japanese Application No. 2013-197687.
Nov. 5, 2015 Office Action issued in U.S. Appl. No. 14/314,473.
Aug. 29, 2015 Partial Search Report issued in European Application No. 14173724.7.
U.S. Appl. No. 14/314,473, filed Jun. 25, 2014.
Nov. 6, 2015 Office Action issued in U.S. Appl. No. 14/314,657.
Aug. 1, 2014 Extended Search Report issued in European Application No. 14173720.5.
U.S. Appl. No. 14/314,657, filed Jun. 25, 2014.
Feb. 26, 2016 Office Action issued in Japanese Patent Application No. 2013-197687.

* cited by examiner

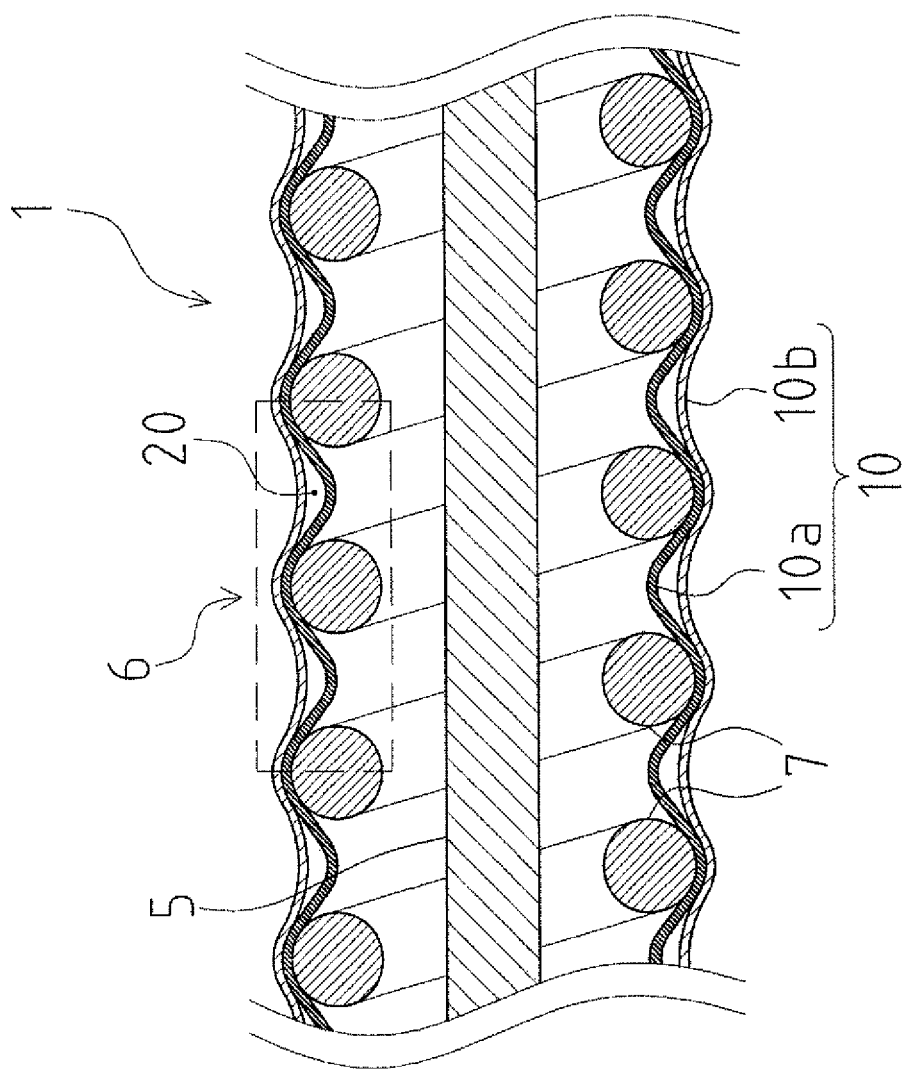

GUIDEWIRE

CROSS-REFERENCE TO RELATED APPLICATION

This application claims priority to Japanese Application No. 2013-197686 which was filed on Sep. 25, 2013, the entire contents of which is hereby incorporated by reference.

BACKGROUND

The disclosed embodiments relate to a medical device. Specifically, the disclosed embodiments relate to a guide wire that is inserted into a lumen such as a blood vessel.

A guide wire used when inserting a catheter into a blood vessel is known. When inserting a catheter, the guide wire is first inserted into the blood vessel, and then the catheter is allowed to proceed along the guide wire. In such manner, the guide wire functions as a guide which guides the catheter to the lesion area.

A so-called coil-type guide wire having the distal end portion of its core shaft covered with a coil body is commonly used as such a guide wire. In addition, for the purpose of increasing lubricity within the blood vessel, a guide wire having the surface of its coil body covered with a hydrophilic coating film has been proposed in U.S. Pat. No 5,840,046 and Japanese Unexamined Patent Application Publication No. 2008-237621. The hydrophilic coating film is capable of exhibiting sufficient lubricity in cases when moisture (such as blood) exists in its surroundings.

SUMMARY

However, with the abovementioned conventional guide wire, in environments where it is difficult for blood to be supplied (environments where there is little moisture surrounding the guide wire), for example, inside the lesion of a chronic total occlusion (CTO), there is a problem of insufficient lubricity being exhibited due to stagnation of the supply of moisture to the hydrophilic coating film.

The disclosed embodiments have been devised in light of the abovementioned problem exhibited by conventional technology and an object of the present invention is to provide technology for a guide wire having its coil body covered with a hydrophilic coating film capable of exhibiting sufficient lubricity even in a situation where there is little moisture in its surroundings.

In order to solve the abovementioned problem, a guide wire according to aspects of the present invention uses the following configuration. Namely, a guide wire comprises a core shaft, a coil body which covers the core shaft, and a coating portion which covers the coil body. The guide wire is characterized in that the coating portion is formed by stacking a plurality of films. The film of the innermost layer of the coating portion is a hydrophobic film, and the film of the layer above the innermost layer of the coating portion is a hydrophilic film. The hydrophobic film is arranged to extend between adjacent coils of the coil body, and a space is formed between the hydrophilic film of the outer layer and the sections where the hydrophobic film extends between the adjacent coils of the coil body.

Here, the "hydrophilic film" of the present invention is not limited to a film formed of a hydrophilic substance (such as a hydrophilic resin), but includes any film that is formed of a hydrophilic substance (such as a hydrophilic resin) and a hydrophobic substance (such as a cross-linking agent) that exhibits hydrophilic properties as a whole depending on the mixing ratio of the substances.

In addition, the "hydrophobic film" of the present invention is not limited to a film formed of a hydrophobic substance (such as a hydrophobic resin), but includes any film that is formed of a hydrophilic substance (such as a hydrophilic resin) and a hydrophobic substance (such as a cross-linking agent) that exhibits hydrophobic properties as a whole depending on the mixing ratio of the substances.

With such a guide wire, as spaces are formed between the hydrophilic film of the outer layer thereof and the sections in which the hydrophobic film are arranged to extend between the adjacent coils of the coil body, it is possible to pool moisture within these spaces. Accordingly, even in an environment where there is little moisture surrounding the guide wire such as inside the lesion of a chronic total occlusion (CTO) and supply of moisture to the hydrophilic film is stagnated, it is possible to supply the moisture pooled in the space to the hydrophilic film. As a result, it becomes possible to sufficiently exhibit lubricity of the hydrophilic film of the guide wire.

In addition, in the abovementioned guide wire, the hydrophilic film of the coating portion may be that of two or more layers while the hydrophilic film of the outer layer has a higher degree of water retentivity than the hydrophilic film of the inner layer.

With such a guide wire, in an environment where there is little moisture in the surroundings, by supplying the moisture pooled in the spaces to the hydrophilic film, it is possible to sufficiently exhibit the lubricity thereof.

In addition, as the hydrophilic film of the coating portion is that of two or more layers while the hydrophilic film of the outer layer has a higher degree of water retentivity than the hydrophilic film of the inner layer, it is possible to ensure that moisture is pooled in the spaces. Accordingly, for example, in a case where the guide wire (and coil body) is largely bent inside a blood vessel, it is possible to suppress the moisture pooled in the spaces from being discharged to the outside. As a result, in a case where moisture surrounding the guide wire decreases, it becomes possible to ensure that moisture is supplied to the hydrophilic film.

In addition, with the guide wire, in cases when the hydrophilic film of the coating portion is that having two or more layers, in the sections where the films of the coating portion are arranged to extend between the adjacent coils of the coil body, spaces may also be formed between the hydrophilic films.

With such a guide wire, not only are spaces formed between the hydrophobic film (film of the innermost layer) and the hydrophilic film, but spaces are also formed between the hydrophilic films of the outer layers thereof. Accordingly, as there are a greater number of spaces, it is possible to pool a greater amount of moisture. As a result, for example, even in a case where a procedure is to be performed for a long period of time in an environment where there is little moisture in the surroundings such as inside the lesion of a chronic total occlusion (CTO), by supplying a sufficient amount of moisture to the hydrophilic film, it becomes possible to continue to exhibit lubricity.

BRIEF DESCRIPTION OF DRAWINGS

FIG. 2 is an enlarged view of the coil body and the coating portion of the guide wire according to an exemplary embodiment of the present invention.

FIG. 3A illustrates a situation where moisture (blood) exists around the guide wire while FIG. 3B illustrates a situation in which the guide wire is placed in an environment where there is little moisture such as inside the lesion of a chronic total occlusion (CTO).

DETAILED DESCRIPTION OF EMBODIMENTS

Figure 1:
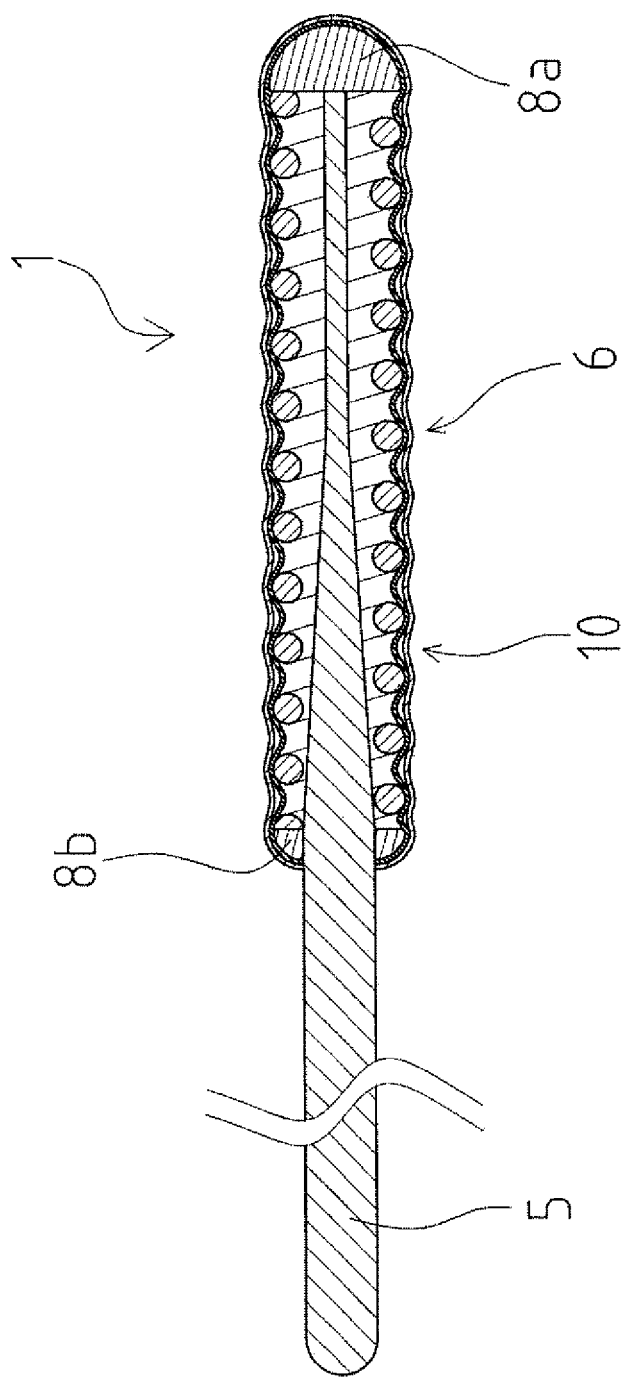
FIG. 1 is an explanatory diagram illustrating the configuration of a guide wire according to an exemplary embodiment of the present invention.

FIG. 1 is an explanatory diagram illustrating the configuration of guide wire (1) according to an exemplary embodiment of the present invention. Guide wire (1) includes a core shaft (5) and coil body (6) which covers the core shaft (5). The core shaft (5) and the coil body (6) are joined to each other via a joint made of a brazing material. In this embodiment, the distal end of the coil body (6) and the distal end of the core shaft (5) are connected via a joint (8a) while the proximal end of coil body (6) and the middle portion of core shaft (5) are connected via a joint (8b).

The surface of the coil body (6) is covered with a coating portion (10). The coating portion (10) is provided in order to ensure lubricity when the guide wire (1) is inserted into a blood vessel by reducing the frictional resistance between the surface of the guide wire (1) and the inner walls of the blood vessel.

FIG. 2 is an enlarged view of the coil body (6) and the coating portion (10) of the guide wire (1). As illustrated in FIG. 2, the coil body (6) of the guide wire (1) is formed in a so-called open-coiled shape where adjacent wires (7) (or coils (7)) are not in contact with each other.

Furthermore, coating portion (10) on the surface of the coil body (6) is formed by stacking a plurality of films including an inner layer film (10a) and an outer layer film (10b).

In this configuration, the inner layer film (10a) is a hydrophobic film and the outer layer film (10b) is a hydrophilic film. In FIG. 2, the hydrophobic film (inner layer film (10a)) is illustrated as a film with a dark hatching while the hydrophilic film (outer layer film (10b)) is illustrated as a film with a light hatching. Furthermore, the inner layer film (10a) of the coating portion (10) is arranged to come between the wires of the coil body (6) and a space (20) is formed between the outer layer film (10b) and the sections where the inner layer film (10a) is arranged to come between the wires of coil body (6). More specifically, space (20) is formed between the inner layer film (10a) and the outer layer film (10b) in the areas between adjacent coils of the coil body (6).

The hydrophobic inner layer film (10a) of this embodiment may be formed using, for example, a polyurethane-based resin, a polystyrene-based resin, a polyester-based resin, a polyamide-based resin, an acrylate-based resin, a polyethylene-based resin, a fluorine-based resin, carbodiimide, or a cellulose-based polymer. In addition, the inner layer film (10a) may be formed using, for example, a monomer of methyl methacrylate, vinyl acetate, vinyl laurate, or vinyl stearate or a copolymer thereof. Furthermore, the inner layer film (10a) may also be formed as a mixture of the abovementioned materials.

In addition, the hydrophilic outer layer film (10b) of this embodiment may be formed with, for example, polyvinyl alcohol, polyvinyl pyrrrolidone, polyethylene glycol, polyacrylamide, polyacrylic acid, sodium polyacrylate, poly-(2-hydroxyethyl methacrylate), a maleic acid copolymer, an ethylene vinyl alcohol copolymer, a monomer of 2-methacryloyloxyehtyl phosphorylcholine or a copolymer thereof, a (2-hydroxyethyl methacrylate)-styrene block copolymer, various synthetic polypeptides, collagen, hyaluronic acid, a cellulose-based polymer, or a mixture of any of these.

Furthermore, the hydrophobic inner layer film (10a) of this embodiment may be a composition that includes a hydrophilic material (for example, polyvinyl alcohol) and a hydrophobic material (for example, a cross-linking agent such as carbodiimide) and exhibits a hydrophobic property as a whole due to the mixing ratio of the hydrophobic material being high.

In addition, the hydrophilic outer layer film (10b) of this embodiment may be a composition that includes a hydrophilic material (for example, polyvinyl alcohol) and a hydrophobic material (for example, a cross-linking agent such as carbodiimide) and exhibits a hydrophilic property as a whole due to the mixing ratio of the hydrophilic material being high.

Figure 3A:
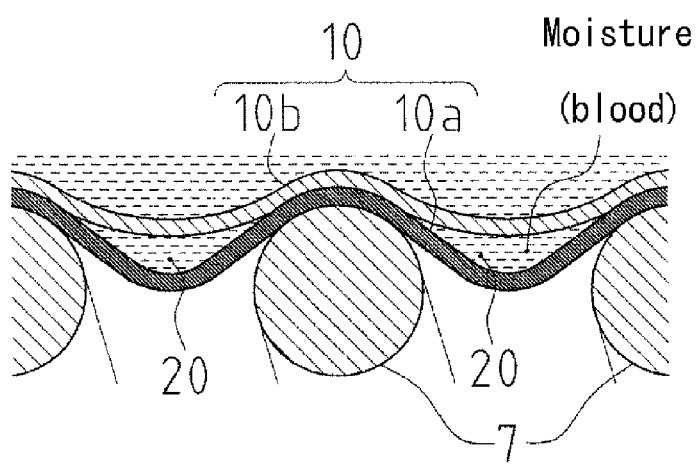
FIGS. 3A and 3B are explanatory diagrams illustrating the function of the spaces of the guide wire according to an exemplary embodiment of the present invention. Enlarged views of the section outlined by the dotted line in FIG. 2 are illustrated in FIGS. 3A and 3B. Furthermore.
Figure 3B:
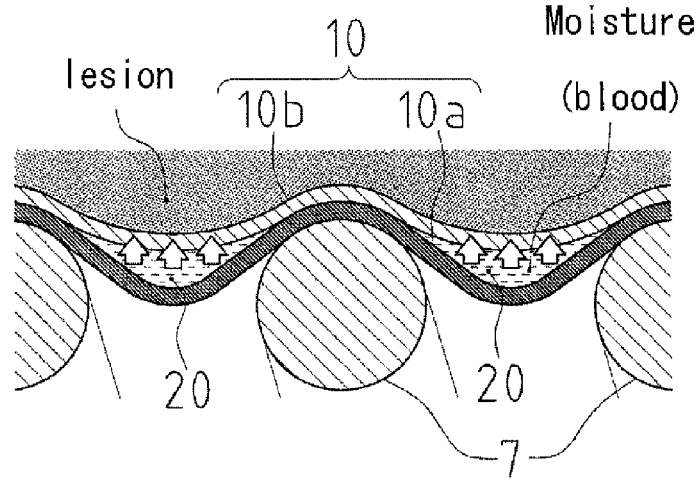

FIGS. 3A and 3B are explanatory diagrams illustrating the function of the space (20) of the guide wire (1). Enlarged views of the section outlined by the dotted line in FIG. 2 are illustrated in FIGS. 3A and 3B. Furthermore, FIG. 3A illustrates a situation where moisture (blood) exists around the guide wire (1) while FIG. 3B illustrates a situation in which the guide wire (1) is placed in an environment where there is little moisture such as inside the lesion of a chronic total occlusion (CTO).

As illustrated in FIG. 3A, when moisture (blood) exists around the guide wire (1), moisture is constantly supplied to the hydrophilic outer layer film (10b), and lubricity of the outer layer film (10b) is exhibited. In addition, a part of this moisture (blood) permeates the hydrophilic outer layer film (10b) and stays pooled in the space (20).

Meanwhile, as illustrated in FIG. 3B, when the guide wire (1) exists in an environment where there is little moisture such as inside the lesion of a chronic total occlusion (CTO), there is almost no supply of moisture to the hydrophilic outer layer film (10b) from the outside. However, because moisture is pooled in the space (20) of the coating portion (10), this moisture is supplied to the hydrophilic outer layer film (10b). As a result, even when the guide wire (1) is placed in an environment where there is little moisture in its surroundings, it is possible for the hydrophilic outer layer film (10b) to exhibit sufficient lubricity.

The above explains the function of the space (20) in a case where the guide wire (1) is inserted, for example, inside the lesion of a chronic total occlusion (CTO). However, there are cases other than that mentioned in the above. For example, there is a case where the guide wire (1) is temporarily removed from the blood vessel during the procedure. Here, due to the moisture around guide wire (1) no longer existing, the supply of moisture to the hydrophilic film (outer layer film (10b)) from the outside ceases to exist.

Even in such a case, because the moisture pooled in the space (20) of the coating portion (10) is supplied to the hydrophilic outer layer film (10b), it is possible for the hydrophilic outer layer film (10b) to exhibit sufficient lubricity.

In addition, in a procedure where the guide wire (1) and a catheter are used together and are inserted into a flexure of a blood vessel, the coating portion (10) of the guide wire (1) is pressed strongly against the inner walls of the catheter. As a result, it is possible that the moisture contained in the hydrophilic film (outer layer film (10b)) is discharged to the outside.

Even in such case, by the moisture pooled in the space (20) of the coating portion (10) being supplied to the hydrophilic outer layer film (10b), it becomes possible for the hydrophilic outer layer film (10b) to exhibit sufficient lubricity.

Modifications of the guide wire (1) as described above may also be considered. It shall be noted that in the following explanations, components that are identical to guide wire (1) of the embodiment described above are noted with the same reference numbers and detailed explanations thereof are omitted.

Figure 4:
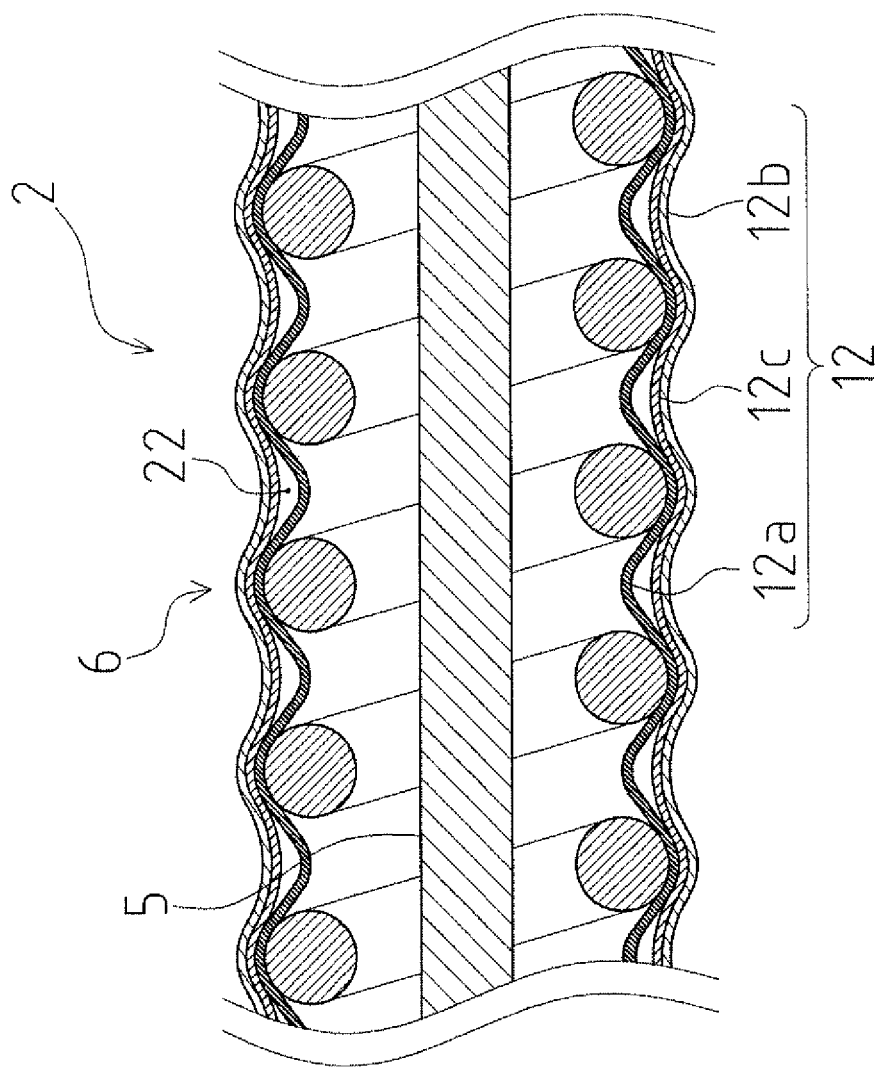
FIG. 4 is an enlarged view of the coil body and the coating portion of a guide wire according to an exemplary embodiment of the present invention.

FIG. 4 is an enlarged view of the coil body (6) and a coating portion (12) of a guide wire (2). The coating portion (12) which covers the coil body (6) is configured of three layers of films including an inner layer film (12a), a middle layer film (12c), and an outer layer film (12b). Of these films, the inner layer film (12a) is formed of a hydrophobic film while the middle layer film (12c) and the outer layer film (12b) are formed of a hydrophilic film.

The outer layer film (12b) is formed of a material having a higher degree of water retentivity than the middle layer film (12c). In FIG. 4, a lighter hatching than that identifying the middle layer film (12c) is used to identify the outer layer film (12b). By this nomenclature, it is illustrated that the water retentivity of the outer layer film (12b) is higher than that of the middle layer film (12c).

As one example, a hydrophilic polyvinyl alcohol is used for the middle layer film (12c), and a hydrophilic hyaluronic acid having a high degree of water retentivity is used for the outer layer film (12b).

The guide wire (2) is similar to the guide wire (1) in that the core shaft (5) is inserted through the bore of coil body (6). In addition, a space (22) for pooling moisture is formed between the middle layer film (12c) and the sections where the inner layer film (12a) of the coating portion (12) is arranged to come between wires (7) (adjacent coils) of coil body (6).

In an environment where there is little moisture in the surrounding thereof, the guide wire (2) supplies the moisture pooled in the space (22) to the hydrophilic outer layer film (12b). Therefore, it is possible for the hydrophilic outer layer film (12b) to exhibit sufficient lubricity.

In addition, because the hydrophilic film of the coating portion (12) is multi-layered (having two layers in this embodiment) and the outer layer film (12b) has a higher retentivity than the middle layer film (12c), it is possible to ensure that the moisture pooled in the space (22) stays pooled within the space (22).

For example when the guide wire (2) (and the coil body (6)) is bent within a blood vessel, the moisture is inclined to be pushed outside from within the space (22) due to the deformation of the space (22). Even in such a case, due to the high degree of water retentivity of outer layer film (12b), it is possible to ensure that the moisture of the space (22) stays pooled within the space (22). As a result, when the amount of moisture surrounding the guide wire (2) is reduced, it is possible to ensure that moisture is supplied to the hydrophilic outer layer film (12b).

Figure 5:
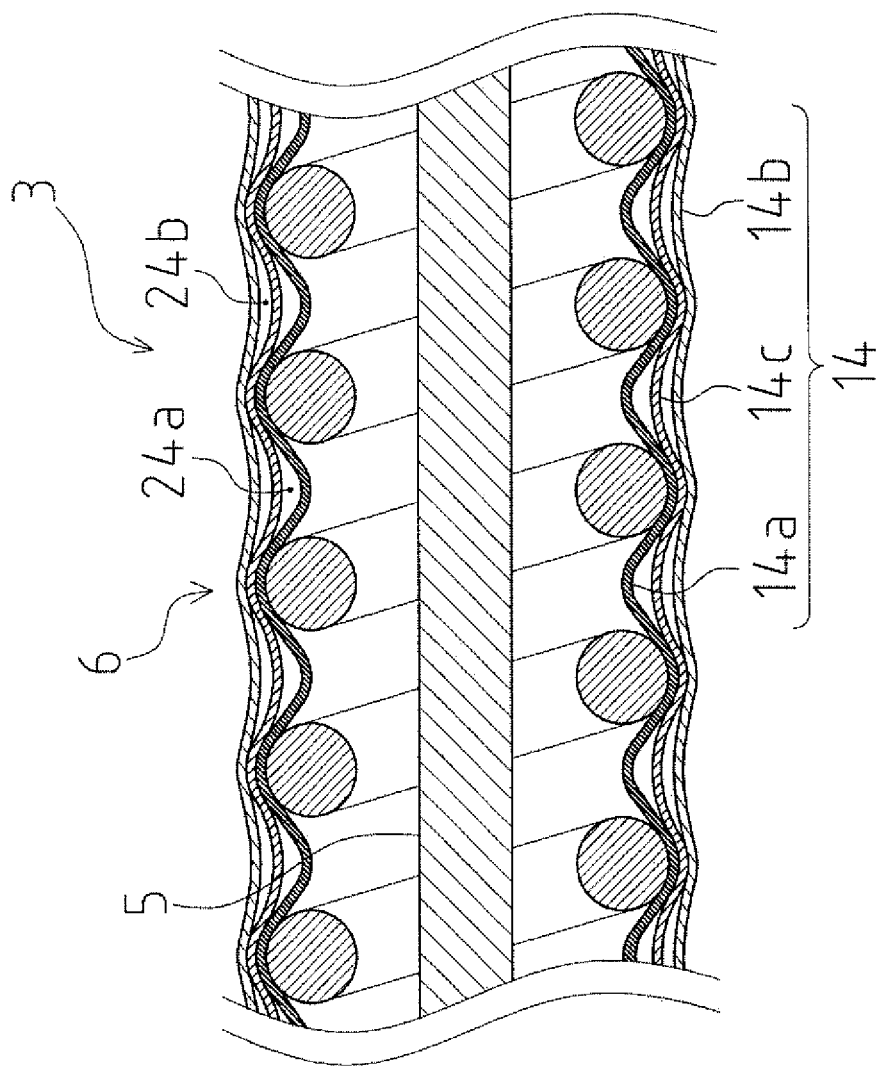
FIG. 5 is an enlarged view of the coil body and the coating portion of a guide wire according to an exemplary embodiment of the present invention.

FIG. 5 is an enlarged view of the coil body (6) and a coating portion (14) of a guide wire (3). The coating portion (14) is of a structure having three layers including a hydrophobic inner layer film (14a), a hydrophilic middle layer film (14c), and a hydrophilic outer layer film (14b). In addition, the core shaft (5) is inserted through the bore of the coil body (6).

Here, not only is a space (24a) formed between the inner layer film (14a) and the middle layer film (14c), but a space (24b) is also formed between the middle layer film (14c) and the outer layer film (14b).

Similar to the abovementioned guide wire (1) and guide wire (2), in an environment where there is little moisture in the surrounding thereof, the guide wire (3) supplies the moisture pooled in spaces (24a, 24b) to the hydrophilic outer layer film (14b). Therefore, it is possible for the hydrophilic outer layer film (14b) to exhibit sufficient lubricity.

Further, because the space (24b) is formed between the middle layer film (14c) and the outer layer film (14b) in addition to the space (24a) being formed between the inner layer film (14a) and the middle layer film (14c), it is possible for a greater amount of moisture to be pooled in the spaces. As a result, even in a case where a procedure is to be performed for a long period of time in an environment where there is little moisture, such as inside the lesion of a chronic total occlusion (CTO), it is possible for the hydrophilic outer layer film (14b) to exhibit sufficient lubricity. This is done by continuing to supply moisture from the spaces (24a) and (24b) to the hydrophilic outer layer film (14b).

In guide wire (3), the outer layer film (14b) is lifted up by the two spaces (spaces (24a, 24b)), and, due to this, the surface of the outer layer film (14b) is a surface having a very small amount of unevenness. Accordingly, as it is possible to prevent the outside of the outer layer film (14b) from catching on a blood vessel wall, it becomes possible to improve lubricity within a blood vessel.

Although a guide wire including various modifications is explained above, the present invention is not limited to the abovementioned description, and it is possible for the present invention to be implemented in various manners without departing from the invention. For example, the hydrophilic film of the coating portion was explained as a film having one or two layers (refer to FIG. 2 through FIG. 5). However, this hydrophilic film may have three or more layers (drawing omitted).

Understandably, if the number of hydrophilic films is too many, there is the possibility that such will inhibit the intake of moisture within the space. Therefore, as described above, it is preferable that the hydrophilic film of the coating portion has one or two layers.

In addition, the coil body was explained above as being formed in a so-called open-coiled shape where adjacent wires (adjacent loops of the coil) are not in contact with each other. However, the coil body may be formed in a so-called close-coiled shape where adjacent wires are in contact with each other (drawing omitted).

However, because an open-coiled coil body allows for larger spaces to be formed, more moisture to supply to the hydrophilic film of the coating portion may be pooled in spaces of an open-coiled guide wire. Therefore, as described above, it is preferable that the coil body is formed to be open-coiled.

What is claimed is:
1. A guide wire, comprising:
a core shaft;
a coil body having a plurality of coils and which covers the core shaft, each of the coils of the coil body is spaced apart from adjacent coils so as not to contact the adjacent coils; and
a coating portion which covers the coil body and which extends between the adjacent coils of the coil body, the coating portion being formed by a plurality of layers that are stacked on each other, wherein the plurality of layers comprises:

an innermost layer comprising a hydrophobic film that extends continuously over an outer periphery of the coil body including over gaps between the adjacent coils; and an outer layer comprising a hydrophilic film that extends continuously over an outer periphery of the innermost layer; and a first space is formed between the outer layer and the innermost layer only in areas that extend between the adjacent coils of the coil body.

2. The guide wire according to claim 1, wherein:

the outer layer comprises at least two layers, each of the at least two layers comprising a hydrophilic film; and a second space is formed between layers of the outer layer at axial positions of the guide wire corresponding to the portions of the innermost layer that extend between the adjacent coils of the coil body.

3. The guide wire according to claim 2, wherein:

an outermost layer of the at least two layers of the outer layer has a higher degree of water retentivity than other layers of the outer layer.

* * * * *